(12) United States Patent
Gold et al.

(10) Patent No.: US 10,736,855 B2
(45) Date of Patent: Aug. 11, 2020

(54) COMPOSITIONS COMPRISING PROTON PUMP INHIBITORS

(71) Applicant: DEXCEL PHARMA TECHNOLOGIES LTD., Or-Akiva (IL)

(72) Inventors: Tomer Gold, Herzliya (IL); Irit Ventura, Zichron Yaacov (IL)

(73) Assignee: DEXCEL PHARMA TECHNOLOGIES LTD., Or-Akiva (IL)

(*) Notice: Subject to any disclaimer, the term of this patent is extended or adjusted under 35 U.S.C. 154(b) by 0 days.

(21) Appl. No.: 16/078,343

(22) PCT Filed: Feb. 13, 2017

(86) PCT No.: PCT/IL2017/050179
§ 371 (c)(1),
(2) Date: Aug. 21, 2018

(87) PCT Pub. No.: WO2017/145146
PCT Pub. Date: Aug. 31, 2017

(65) Prior Publication Data
US 2019/0046457 A1  Feb. 14, 2019

Related U.S. Application Data

(60) Provisional application No. 62/299,764, filed on Feb. 25, 2016.

(51) Int. Cl.
*A61K 9/50* (2006.01)
*A61K 31/4439* (2006.01)
*A61K 9/00* (2006.01)
*A61K 9/10* (2006.01)

(52) U.S. Cl.
CPC .......... *A61K 9/5047* (2013.01); *A61K 9/0095* (2013.01); *A61K 9/10* (2013.01); *A61K 9/5036* (2013.01); *A61K 9/5042* (2013.01); *A61K 31/4439* (2013.01)

(58) Field of Classification Search
CPC .......................... A61K 31/4439; A61K 9/5047
See application file for complete search history.

(56) References Cited

U.S. PATENT DOCUMENTS

| | | |
|---|---|---|
| 4,045,563 A | 8/1977 | Berntsson et al. |
| 4,255,431 A | 3/1981 | Junggren et al. |
| 4,359,465 A | 11/1982 | Ruwart |
| 4,472,409 A | 9/1984 | Senn-Bilfinger |
| 4,508,905 A | 4/1985 | Junggren et al. |
| 4,628,098 A | 12/1986 | Nohara et al. |
| 4,738,975 A | 4/1988 | Nohara et al. |
| 4,786,505 A | 11/1988 | Lovgren et al. |
| 4,853,230 A | 8/1989 | Lovgren et al. |
| 4,882,169 A | 11/1989 | Ventouras |
| 5,045,321 A | 9/1991 | Makino et al. |
| 5,045,552 A | 9/1991 | Souda et al. |
| 5,312,824 A | 5/1994 | Sohda et al. |
| 5,690,960 A | 11/1997 | Bengtsson et al. |
| 5,714,504 A | 2/1998 | Lindberg et al. |
| 5,900,424 A | 5/1999 | Kallstrom et al. |
| 6,147,103 A | 11/2000 | Anousis et al. |
| 6,149,942 A | 11/2000 | Scheiwe et al. |
| 6,166,213 A | 12/2000 | Anousis et al. |
| 6,191,148 B1 | 2/2001 | McManus et al. |
| 6,228,400 B1 | 5/2001 | Lee et al. |
| 6,248,355 B1 | 6/2001 | Seth |
| 6,316,481 B1 | 11/2001 | Freehauf |
| 6,328,993 B1 | 12/2001 | Linder et al. |
| 6,328,994 B1 | 12/2001 | Shimizu et al. |
| 6,369,085 B1 | 4/2002 | Cotton et al. |
| 6,391,342 B1 | 5/2002 | Henriksen et al. |
| 6,428,810 B1 | 8/2002 | Bergstrand et al. |
| 6,479,075 B1 | 11/2002 | Odidi et al. |
| 6,551,621 B1 | 4/2003 | Debregeas et al. |
| 6,576,258 B1 | 6/2003 | Kofler et al. |
| 6,596,315 B1 | 7/2003 | Boissier et al. |
| 6,605,303 B1 | 8/2003 | Karehill et al. |
| 6,610,323 B1 | 8/2003 | Lundberg et al. |
| 6,706,285 B1 | 3/2004 | Woo |
| 6,780,436 B1 | 8/2004 | López-Cabrera et al. |
| 6,780,882 B2 | 8/2004 | Phillips |
| 7,041,316 B2 | 5/2006 | Chen |

(Continued)

FOREIGN PATENT DOCUMENTS

| | | |
|---|---|---|
| EP | 1232746 A1 | 8/2002 |
| EP | 1949900 A2 | 7/2008 |

(Continued)

OTHER PUBLICATIONS

Kollidon (https://industries.basf.com/bin/bws/docunnentDownload.en.8800483977685) BASF Mar. 2008, 9th revised edition, pp. 1-330 (Year: 2008).*

(Continued)

*Primary Examiner* — Andrew S Rosenthal
(74) *Attorney, Agent, or Firm* — Rothwell, Figg, Ernst & Manbeck, P.C.

(57) ABSTRACT

A composition suitable for forming a viscous suspension upon admixing with an aqueous medium, methods for its production and use thereof are provided. The composition includes a plurality of units, each unit having a core containing a proton pump inhibitor and an outer coating containing a gel-forming agent.

24 Claims, 9 Drawing Sheets

(56) References Cited

U.S. PATENT DOCUMENTS

| | | | |
|---|---|---|---|
| 7,217,429 B2 | 5/2007 | Garcia et al. | |
| 7,276,253 B2 | 10/2007 | Heese et al. | |
| 7,419,996 B2 | 9/2008 | Chow et al. | |
| 7,732,474 B2 | 6/2010 | Muskulus et al. | |
| 7,906,145 B2 | 3/2011 | Castan et al. | |
| 8,530,500 B2 | 9/2013 | Juvonen et al. | |
| 8,968,776 B2 | 3/2015 | Seth et al. | |
| 8,993,599 B2 | 3/2015 | Hall et al. | |
| 2001/0053387 A1* | 12/2001 | Hamied | A61K 9/5078 424/474 |
| 2002/0039597 A1 | 4/2002 | Ukai et al. | |
| 2003/0091643 A1 | 5/2003 | Friesen et al. | |
| 2005/0031700 A1 | 2/2005 | Hall et al. | |
| 2005/0042277 A1* | 2/2005 | Srinivas | A61P 1/04 424/452 |
| 2005/0095285 A1 | 5/2005 | Rao et al. | |
| 2006/0093680 A1 | 5/2006 | Humar et al. | |
| 2006/0134210 A1* | 6/2006 | Persson | A61K 9/0014 424/471 |
| 2006/0159756 A1 | 7/2006 | Sjoblom | |
| 2006/0165794 A1 | 7/2006 | Chenevier et al. | |
| 2007/0053981 A1 | 3/2007 | Blychert et al. | |
| 2007/0196486 A1 | 8/2007 | Vanderbist et al. | |
| 2008/0175917 A1 | 7/2008 | Glad et al. | |
| 2009/0068261 A1 | 3/2009 | Reher et al. | |
| 2009/0092658 A1 | 4/2009 | Hall et al. | |
| 2009/0291136 A1 | 11/2009 | Stanic Ljubin et al. | |
| 2010/0068291 A1 | 3/2010 | Caisse et al. | |
| 2011/0223244 A1 | 9/2011 | Liversidge et al. | |
| 2012/0128764 A1 | 5/2012 | Venkatesh et al. | |
| 2013/0202705 A1 | 8/2013 | Hamed | |
| 2013/0266658 A1 | 10/2013 | Weiß et al. | |
| 2014/0065232 A1 | 3/2014 | Shlieout et al. | |
| 2014/0255503 A1 | 9/2014 | Sangrà Perez et al. | |
| 2014/0377347 A1 | 12/2014 | Vivek et al. | |
| 2015/0044303 A1 | 2/2015 | Olmstead et al. | |
| 2015/0209432 A1 | 7/2015 | Konda et al. | |

FOREIGN PATENT DOCUMENTS

| | | | |
|---|---|---|---|
| WO | WO-0078293 A1 * | 12/2000 | A61K 9/0004 |
| WO | WO 2004/004690 A1 | 1/2004 | |
| WO | WO 2005/105045 A1 | 11/2005 | |
| WO | WO 2006/068596 A1 | 6/2006 | |
| WO | WO 2012/017074 A1 | 2/2012 | |
| WO | WO 2015/082562 A1 | 6/2015 | |
| WO | WO 2015/108392 A1 | 7/2015 | |
| WO | WO 2015/166473 A1 | 11/2015 | |

OTHER PUBLICATIONS

Talukdar, M.M. et al. "Swelling and drug release behaviour of xanthan gum matrix tablets" International Journal of Pharmaceutics 120 (1995) 63-72 (Year: 1995).*

Nargund, R. et al. "Synthesis, characterization and antiulcer study of pH-sensitive microspheres" Der Pharmacia Lettre, 2011, 3 (6):82-89 (Year: 2011).*

International Search Report and Written Opinion issued for PCT application No. PCT/IL2017/050179 dated May 9, 2017, 8 pages.

* cited by examiner

COMPOSITIONS COMPRISING PROTON PUMP INHIBITORS

CROSS REFERENCE TO RELATED APPLICATION

This application is a 35 U.S.C. 371 National Phase Entry Application from PCT/IL2017/050179, filed Feb. 13, 2017, which claims the benefit of U.S. Ser. No. 62/299,764 filed on Feb. 25, 2016, the disclosures of which are incorporated herein in its entirety by reference.

TECHNICAL FIELD

A solid dosage form of a proton pump inhibitor, suitable for forming a viscous suspension upon admixing with an aqueous medium, methods for its production and use thereof are provided.

BACKGROUND

There is an increasing need for alternative dosage forms to conventional tablets and capsules. Such alternative dosage forms are, for example, in the form of small particles which can be sprinkled onto food or mixed with liquids to form a suspension that can be readily swallowed. These dosage forms provide improved patient compliance, particularly in patients who exhibit difficulties swallowing conventional dosage forms such as pediatric and geriatric patients, subjects who suffer from impaired swallowing and subjects who suffer from psychiatric disorders.

Formulations suitable for forming suspensions prior to administration are advantageous compared to ready-to-use suspensions, mainly due to their improved stability in storage conditions. A problem that is often encountered with ready-to-use suspensions is the sedimentation or segregation of some of the particles which result in a non-uniform distribution of the active compound. Another problem occurs when the suspension is becoming too viscous thereby being incompatible for oral administration as well as for administration through a nasogastric tube.

Proton pump inhibitors (PPIs) are potent inhibitors of gastric acid secretion by specific inhibition of the $H^+/K^+$-ATPase enzyme system at the secretory surface of the gastric parietal cells. They are used for the treatment of gastric and duodenal ulcers, gastroesophageal reflux disease and other excessive gastrointestinal acid secretory disorders. PPIs are typically benzimidazole derivatives such as omeprazole, lansoprazole, and pantoprazole. U.S. Pat. Nos. 4,045,563; 4,255,431; 4,359,465; 4,472,409; 4,508,905; 4,628,098; 4,738,975; 4,786,505; 4,853,230; 5,045,321; 5,045,552; and 5,312,824 disclose benzimidazole compounds which can be used as proton pump inhibitors and compositions comprising same.

WO 2006/068596 describes a solid oral pharmaceutical dosage form comprising: (a) a multitude of enteric coated pellets, wherein each enteric coated pellet comprises an acid sensitive proton pump inhibitor, and (b) a suspension modifying granulate comprising a rapidly dissolving diluent, a gelling agent which is a xanthan gum, an acidic pH-regulating agent, a binder, and optionally, a disintegrant, wherein the dosage form is a rapidly-gelling granulate mixture, with the proviso that the granulate is free from bicarbonate and carbonate salts.

EP 1949900 describes a controlled release formulation of solid products for oral administration adapted for preparing single dose sachets, comprising very little pellets with controlled and/or retarded release, consisting of inert granules with size between 250 and 600 µm, covered with an active ingredient having a size between 1 and 200 µm, in turn covered by a membrane adapted to give the controlled release, to obtain pellets for direct administration having a final size between 425 and 710 µm.

EP 1232746 describes readily suspendible dry powder mixture composition comprising a gellant or thickener, comprising at least one xanthan gum having a specific particle size distribution, a filler, a wetting agent or surfactant, and a pharmacologically active substance. EP 1232746 further describes the use of the dry powder mixture composition for the preparation of a suspension of the active substance and to liquid or semi-liquid pharmaceutical compositions comprising a suspension of an active substance.

WO 2004/004690 describes a liquid dosage form having enteric coated microgranules comprising an acid-labile drug and a liquid suspension having a pH less than 6.0 and a viscosity sufficient to suspend the microgranules. Carbonates or bicarbonates may be used in the dosage forms.

There is an unmet need for a PPI composition in the form of small particles which is suitable for forming a viscous suspension upon admixing with a liquid for oral administration.

SUMMARY

The present disclosure relates to a composition suitable for forming a viscous suspension upon admixing with an aqueous medium. The composition comprises a plurality of units, each unit comprises: i) a core comprising a proton pump inhibitor; and ii) an outer coating comprising a gel-forming agent, wherein the core is overcoated with the outer coating.

Surprisingly, it has now been found that by applying an outer coating comprising a gel-forming agent to a core comprising a PPI, a composition suitable for forming a viscous suspension upon admixing with an aqueous medium is obtained. The thus formed suspension is characterized by viscosity suitable for oral administration as well as for administration through a nasogastric tube.

According to one embodiment, the plurality of units swells upon imbibition of the aqueous medium by at least 50% of its initial volume prior to admixing with the aqueous medium. According to another embodiment, the plurality of units swells upon imbibition of the aqueous medium by at least 100% of its initial volume prior to admixing with the aqueous medium. According to yet another embodiment, the plurality of units swells upon imbibition of the aqueous medium by at least 150% of its initial volume prior to admixing with the aqueous medium.

In several embodiments, the proton pump inhibitor comprises at least one of omeprazole, lansoprazole, pantoprazole, rabeprazole, tenatoprazole and pharmaceutically acceptable salts thereof. Each possibility represents a separate embodiment.

It is contemplated that any pharmaceutically acceptable form of the proton pump inhibitor including, but not limited to, salts (e.g. alkaline salts), solvates (e.g. hydrates), isomers, isomorphs, polymorphs, pseudopolymorphs, and prodrugs thereof are within the scope of the present disclosure.

In one embodiment, the proton pump inhibitor comprises a proton pump inhibitor salt.

In another embodiment, the proton pump inhibitor comprises a proton pump inhibitor enantiomer.

In further embodiments, the proton pump inhibitor comprises a salt of a proton pump inhibitor enantiomer.

In specific embodiments, the salt of a proton pump inhibitor enantiomer is esomeprazole magnesium.

In some embodiments, the core comprises an inert seed coated with a drug layer comprising a proton pump inhibitor.

In other embodiments, the inert seed comprises a sugar sphere. In yet other embodiments, the inert seed comprises microcrystalline cellulose. In additional embodiments, the inert seed comprises a lactose sphere.

In various embodiments, the core comprises an enteric coating over the drug layer. In particular embodiment, the enteric coating is selected from the group consisting of cellulose acetate phthalate (CAP), hydroxypropyl methylcellulose phthalate (HPMCP), hydroxypropyl methylcellulose acetate succinate (HPMCAS), polyvinyl acetate phthalate, cellulose acetate trimellitate, shellac, polymethacrylic acid, polymethyl methacrylate, polyethyl methacrylate, polyethyl acrylate and mixtures thereof, with each possibility representing a separate embodiment. In one embodiment, the enteric coating comprises hydroxypropyl methylcellulose phthalate.

In certain embodiments, the core may further comprise a subcoating to protect the enteric coating from reacting with the alkaline environment surrounding the proton pump inhibitor. In some embodiments, the subcoating comprises at least one of hydroxypropyl methylcellulose, hydroxypropyl cellulose, polyvinylpyrrolidone, polyethylene glycol, polyvinyl alcohol and mixtures thereof, with each possibility representing a separate embodiment.

In additional embodiments, the plurality of units may optionally comprise an additional taste-masking layer typically layered over the enteric coating, if present, the taste-masking layer comprising a substantially water-insoluble taste-masking polymer. In particular embodiments, the substantially water-insoluble taste-masking polymer comprises at least one of ethyl cellulose, polyvinyl acetate (PVA), cellulose acetate (CA), cellulose acetate butyrate (CAB), and methacrylate copolymers including dimethylaminoethyl methacrylate, butyl methacrylate, methyl methacrylate copolymers such as those available under the trade name "Eudragit®" (e.g. Eudragit® RL, Eudragit® RS, Eudragit® E, Eudragit® NE30D, etc.), with each possibility representing a separate embodiment.

In certain embodiments, the gel-forming agent in the outer coating comprises at least one of a polysaccharide, an acrylic or methacrylic polymer, a cellulose derivative; polyethylene glycol, alginic acid, sodium alginate, carbomer, gelatin, magnesium aluminum silicate, poloxamer, polyvinyl alcohol, and naturally occurring or synthetic gum, with each possibility representing a separate embodiment.

In one embodiment, the naturally occurring or synthetic gum is selected from the group consisting of xanthan gum, gum arabic, guar gum, locust bean gum, and gellan gum, with each possibility representing a separate embodiment.

In particular embodiments, the naturally occurring or synthetic gum comprises xanthan gum.

It is contemplated that each of the plurality of units may further comprise a pharmaceutically acceptable excipient. Suitable pharmaceutically acceptable excipients include, but are not limited to, a binder, a filler, a surfactant, an anti-tacking agent, a plasticizer, a lubricant, a glidant, a disintegrant, an alkaline substance, a diluent, a tonicity enhancing agent, a wetting agent, a buffering substance, a colorant, a preservative and any combination thereof, with each possibility representing a separate embodiment. It will be recognized by one of skill in the art that the pharmaceutically acceptable excipient may be the inert seed and/or it may be present in the drug layer, subcoating, enteric coating, taste-masking or outer coating together with other substances constituting these layers, with each possibility representing a separate embodiment.

In one embodiment, the composition comprises a plurality of units, as described herein, as a single population. In other embodiments, the composition comprises a plurality of units, as described herein, as a first population, and a plurality of particles as a second population. In various embodiments, the plurality of particles of the second population is selected from granules, inert pellets, beads, powder, and mixtures thereof, with each possibility representing a separate embodiment. In one embodiment, the plurality of particles of the second population comprises a gel-forming agent. It will be recognized by one of skill in the art that the gel-forming agent of the plurality of particles of the second population can be the same or different from the gel-forming agent of the outer coating of the first population, with each possibility representing a separate embodiment. Accordingly, it is contemplated that any of the aforementioned gel-forming agents of the outer coating of the first population are suitable for use as gel-forming agents in the second population.

In several embodiments, the plurality of particles which constitutes the second population comprises a gel-forming agent and a pharmaceutically acceptable excipient such as, but not limited to, a binder, a filler, a surfactant, an anti-tacking agent, a plasticizer, a lubricant, a glidant, a disintegrant, an alkaline substance, a diluent, a tonicity enhancing agent, a wetting agent, a buffering substance, a colorant, a preservative, and any combination thereof, with each possibility representing a separate embodiment.

In various embodiments, provided herein is a method of preparing the composition of the disclosure, the method comprising the step of applying an outer coating comprising a gel-forming agent to a plurality of cores comprising a therapeutically effective amount of a proton pump inhibitor thereby obtaining a plurality of units.

It is contemplated that when the composition of the disclosure contains two populations comprising a plurality of units as a first population and a plurality of particles as a second population, the method of preparing the composition of the disclosure further comprises the step of admixing the plurality of units with a plurality of particles comprising a gel-forming agent.

The composition disclosed herein may be adapted for preparing a single dose sachet. In some embodiments, the composition is adapted for administration via the oral route or a nasogastric tube. Each possibility represents a separate embodiment. In accordance with these embodiments, the composition is designed to afford a viscous suspension upon admixture with an aqueous medium. In certain embodiments, the viscous suspension is characterized by viscosity of at least about 0.01 Pascal-seconds (Pa s), for example between about 0.01 to about 1,000, or between about 0.01 to about 100, or between about 0.01 to about 50, or between about 0.01 to about 20, or between about 0.1 to about 15, or between about 1 to about 10 Pascal-seconds (Pa s), including each integer within the specified range. Each possibility represents a separate embodiment.

In certain embodiments, the viscosity of the formed suspension is sufficient to prevent sedimentation or segregation of solids suspended therein.

The composition disclosed herein is useful for inhibiting gastric acid secretion in the treatment of gastroesophageal reflux disease, gastritis, peptic ulcers (duodenal and gastric), and erosive esophagitis, with each possibility representing a separate embodiment.

Accordingly, provided herein is a method of treating a disease or disorder selected from the group consisting of gastroesophageal reflux disease, gastritis, peptic ulcers (duodenal and gastric), and erosive esophagitis, the method comprising administering to a subject in need thereof the composition disclosed herein.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

Figure 1:
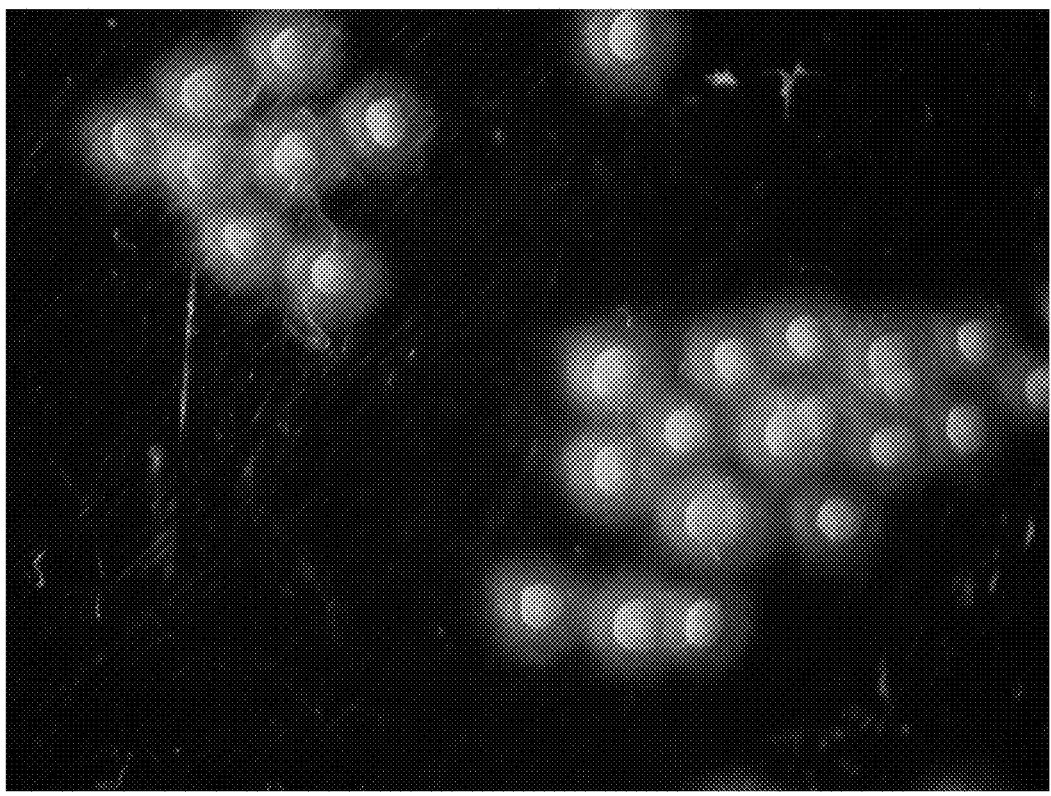
FIG. 1. A micrograph showing a plurality of units according to the disclosure as set forth in Table 2 after admixture with tap water.

There is provided a composition which is a multi-unit dosage form wherein each unit comprises a core comprising a PPI and an outer coating comprising a gel-forming agent over the core. Typically, the core comprises a PPI which is coated with an enteric coating. Upon admixture of the composition with an aqueous medium, each unit swells upon imbibition of the aqueous medium thereby providing an increase in volume of the plurality of units of at least 50%, preferably at least 100%, and more preferably at least 150% of the initial volume such that the final volume occupied by the units is at least 150%, preferably at least 200%, and more preferably at least 250% of the initial volume prior to admixture with the aqueous medium. It is contemplated that upon admixture of the units with an aqueous medium, the outer coating comprising a gel-forming agent of each unit swells upon imbibition of the aqueous medium while the cores remain unaffected. This swelling of the outer coating results in an increase in diameter of each unit (cores and outer coating) by at least 50% of the initial diameter thereby increasing the volume occupied by the plurality of units by at least 50% of the initial volume.

As disclosed herein, there is provided a composition, e.g. a dry particulate composition, suitable for admixing with an aqueous medium to form a viscous suspension. The composition disclosed herein affords several advantages over a ready-to-use suspension. First, it has advantageous stability and storage characteristics. It also avoids the known problem of ready-to-use suspensions in which at least some of the solid particles sink to the bottom of the vessel thereby resulting in undesirable fluctuations in the amount of active ingredient being administered.

The suspension formed upon admixing the composition disclosed herein with an aqueous medium is easily swalloable and more compliant to patients, mainly pediatric and geriatric, that encounter difficulties in swallowing conventional solid dosage forms. Within the scope of the disclosure is the administration of the thus formed suspension using a gastric tube, including a naso-gastric tube which typically requires a formulation having suitable viscosity and viscoelastic properties, as well as the absence of agglomeration of solid particles.

It was not previously realized that cores comprising a therapeutically effective amount of a PPI can be overcoated with a gel-forming agent (e.g. xanthan gum) as an outer coating such that upon admixing with an aqueous liquid, the gel-forming agent dissipates (at least in part) into the aqueous liquid to form a viscous medium, suitable for suspending a particulate matter (e.g. active cores containing the proton pump inhibitor). The composition disclosed herein is more compact and lightweight, particularly compatible with the end user.

According to the principles disclosed herein, the composition comprises a plurality of units, each unit comprises a core comprising a proton pump inhibitor. The cores may have any form including, but not limited to, granules, pellets, beads and the like, with each possibility representing a separate embodiment.

In one embodiment, the proton pump inhibitor is embedded in one or more pharmaceutically acceptable excipients such as a filler (e.g. lactose), a binder (e.g., polyvinylpyrrolidone) and/or an alkalizing agent (e.g., sodium stearate) etc. through granulation, extrusion and spheronization techniques. In accordance with these embodiments, the proton pump inhibitor is surrounded by a matrix of one or more pharmaceutically acceptable excipients.

In another embodiment, the core comprises an inert seed onto which an active coating is applied. The inert seed of the compositions described herein can be comprised of any pharmaceutically inert compound, e.g., a filler. Suitable inert seeds may be comprised of a single compound or a plurality of compounds. Typically, the inert seeds comprise at least one of sugars, starch or cellulosic materials and combinations thereof, for example sugar derivatives such as lactose, sucrose, hydrolyzed starch (maltodextrins) or celluloses or mixtures thereof. In one embodiment, the inert seed comprises nonpareil comprising a blend of starch and sugar. The nonpareils, also called sugar spheres, typically comprise spheres composed of sucrose and starch (for example maize starch). In another embodiment, the inert seed comprises microcrystalline cellulose. In yet another embodiment, the inert seed comprises a lactose sphere. According to certain aspects and embodiments, the amount of the inert seeds is in the range of from about 0.5% to about 20% (w/w) of the total weight of the plurality of units, including each integer within the specified range. Preferably, the amount of the inert seeds is in the range of from about 1% to about 15% (w/w) of the total weight of the plurality of units, including each integer within the specified range. In some embodiments, the amount of the inert seeds is about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (w/w) of the total weight of the plurality of units, with each possibility representing a separate embodiment. The total weight of the plurality of units, as used herein, includes the mass of the active ingredient as well as all applied coatings and excipients.

In further embodiments, the cores comprise a first portion of a proton pump inhibitor embedded in a matrix of excipient(s) as described herein which are further coated with a second portion of a proton pump inhibitor so that the combination of the first and second portions constitute a therapeutically effective amount of the proton The proton pump inhibitors suitable as being incorporated in the compositions disclosed herein include, but are not limited to, lansoprazole, omeprazole, pantoprazole, leminoprazole, perprazole, and rabeprazole, with each possibility representing a separate embodiment.

It is contemplated that any pharmaceutically acceptable form of the proton pump inhibitor including, but not limited to, salts (e.g. alkaline salts), solvates (e.g. hydrates), isomers, isomorphs, polymorphs, pseudopolymorphs, and prodrugs thereof are within the scope of the present disclosure.

In certain embodiments, the proton pump inhibitor is present in the composition as a racemic mixture. In other embodiments, the proton pump inhibitor is present in the composition as a single enantiomeric form. In another embodiment, the proton pump inhibitor is present in the composition as a salt. In further embodiments, the proton pump inhibitor is present in the composition as an alkaline earth metal salt of the PPI such as, but not limited to, a calcium or magnesium salt. In several embodiments, the proton pump inhibitor is present in the composition as an amorphous form. In other embodiments, the proton pump inhibitor is present in the composition as a crystalline form. In currently preferred embodiments, the proton pump inhibitor is the S-enantiomer of omeprazole also known as esomeprazole, preferably in the form of a magnesium salt, i.e. esomeprazole magnesium.

According to certain aspects and embodiments, the amount of the proton pump inhibitor is in the range of from about 0.5% to about 20% (w/w) of the total weight of the plurality of units, including each integer within the specified range. Preferably, the amount of the proton pump inhibitor is in the range of from about 1% to about 15% (w/w) of the total weight of the plurality of units, including each integer within the specified range. In some embodiments, the amount of the proton pump inhibitor is about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% (w/w) of the total weight of the plurality of units, with each possibility representing a separate embodiment.

According to other aspects and embodiments, the core comprises an enteric coating to protect the PPI from the acidic environment of the stomach. In one embodiment, the core further comprises a subcoating layered prior to the layering of the enteric coating to separate the active part of the core from the enteric coating. Non-limiting examples of enteric coating materials include cellulose acetate phthalate (CAP), hydroxypropyl methylcellulose phthalate (HPMCP), hydroxypropyl methylcellulose acetate succinate (HPMCAS), polyvinyl acetate phthalate, cellulose acetate trimellitate, shellac, polymethacrylic acid, polymethyl methacrylate, polyethyl methacrylate, polyethyl acrylate and mixtures thereof, with each possibility representing a separate embodiment. Commercially available enteric coatings are sold under the trade name Eudragit® including, but not limited to, Eudragit® L 100 which is a copolymer of methacrylic acid and methyl methacrylate at a ratio of 1:1, Eudragit® L 30 D-55 which is a copolymer of methacrylic acid and ethyl acrylate at a ratio of 1:1, and Eudragit® L 100-55 which is a copolymer of methacrylic acid and ethyl acrylate at a ratio of 1:1. In particular embodiments, the enteric coating comprises hydroxypropyl methylcellulose phthalate (HPMCP).

According to certain aspects and embodiments, the amount of the enteric coating, if present in the composition, is in the range of from about 5% to about 50% (w/w) of the total weight of the plurality of units, including each integer within the specified range. Preferably, the amount of the enteric coating is in the range of from about 10% to about 40% (w/w) of the total weight of the plurality of units, including each integer within the specified range. In some embodiments, the amount of the enteric coating is about 5%, about 7%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, or about 50% (w/w) of the total weight of the plurality of units, with each possibility representing a separate embodiment.

Suitable subcoating may comprise a substance which affords physical separation between the active part of the core which comprises the proton pump inhibitor and the enteric coating. Typically, the subcoating comprises at least one of hydroxypropyl methylcellulose, hydroxypropyl cellulose, polyvinylpyrrolidone, polyethylene glycol, and polyvinyl alcohol, with each possibility representing a separate embodiment.

Typically, the amount of the subcoating, if present in the composition, is in the range of from about 2% to about 30% (w/w) of the total weight of the plurality of units, including each integer within the specified range. Preferably, the amount of the subcoating, if present in the composition, is in the range of from about 5% to about 25% (w/w) of the total weight of the plurality of units, including each integer within the specified range. In some embodiments, the amount of the subcoating is about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% (w/w) of the total weight of the plurality of units, with each possibility representing a separate embodiment.

The multiple units may optionally comprise an additional taste-masking layer. Typically, the taste-masking layer is applied over the enteric coating. A taste-masking layer may be applied in order to improve the organoleptic characteristics of the composition, such that the taste and mouth feel of the composition is acceptable to a subject until the composition is swallowed. In certain embodiments, the taste-masking layer comprises a substantially water-insoluble polymer, The term "water-insoluble polymer" as used herein designates a polymer which has solubility in water of less than about 10 grams, for example about 7.5, about 5, about 2.5, about 1, about 0.5 grams or less in 100 grams of distilled water at 25° C. and 1 atmosphere. Each possibility represents a separate embodiment. In some embodiments, the water-insoluble polymer comprises a polymer which is substantially insoluble in water at neutral or near-neutral environment presented by the saliva of the oral cavity. In one embodiment, the water-insoluble polymer becomes soluble at pH of about 5 or less. In accordance with these embodiments, the water-insoluble polymer can also be termed a reverse enteric polymer referring to pH sensitive polymers, which are insoluble at pH values greater than those found in the stomach i.e. at pH values greater than about 5 while being soluble at acidic pH values. Polymers suitable for taste-masking include, but are not limited to, ethyl cellulose, polyvinyl acetate (PVA), cellulose acetate (CA), cellulose acetate butyrate (CAB), and methacrylate copolymers including dimethylaminoethyl methacrylate, butyl methacrylate, and methyl methacrylate copolymers. Each possibility represents a separate embodiment. Commercially available polymers suitable for taste-masking include "Eudragit®" polymers such as, but not limited to, Eudragit® RL, Eudragit® RS, Eudragit® E, Eudragit® NE30D, etc., with each possibility representing a separate embodiment. In particular embodiments, the taste-masking layer comprises a cellulose derivative, an acrylate based polymer, PVA or any other polymer currently used for this purpose.

According to certain aspects and embodiments, the amount of the taste-masking layer, if present in the composition, is in the range of from about 2% to about 30% (w/w) of the total weight of the plurality of units, including each integer within the specified range. Preferably, the amount of the taste-masking layer, if present in the composition, is in the range of from about 5% to about 25% (w/w) of the total weight of the plurality of units, including each integer within the specified range. In some embodiments, the amount of the taste-masking layer is about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% (w/w) of the total weight of the plurality of units, with each possibility representing a separate embodiment.

In some embodiments, when the cores are comprised of layers (e.g. drug layer over an inert seed, subcoating over the drug layer, enteric coating over the subcoating, and/or taste-masking layer over the enteric coating), the coating layers substantially cover the seeds or the adjacent inner layer onto which they are applied. In various embodiments, the coating layers cover the seeds or the adjacent inner layer onto which they are applied by at least about 25% of the surface area. In particular embodiments, the coating layers cover the seeds or the adjacent inner layer onto which they are applied by at least about 25%, about 30%, about 35%, about 40%, about 45%, about 50%, about 55%, about 60%, about 65%, about 70%, about 75%, about 80%, about 85%, about 90%, about 95%, or about 100% (substantially complete coverage) of the surface area, with each possibility representing a separate embodiment.

According to the principles disclosed herein, the cores are capped with an outer coating comprising a gel-forming agent. In some embodiments, the outer coating reduces the roundness of the particles as compared to the roundness of enteric coated particles having no outer coating.

Upon admixture with the aqueous medium, the gel-forming agent in the outer-coating rapidly imbibes the aqueous medium such that each unit is initially surrounded by a halo indicative of the swelling. This swelling of the outer coating results in an increase in the total volume occupied by the plurality of units by at least 50%, preferably at least 100%, and more preferably at least 150% of the initial volume. Thereafter, it is believed that the gel-forming agent is at least partially released to the aqueous medium to form a viscous suspension in which the units and/or cores are suspended. The viscous suspension is typically characterized by a viscosity of at least about 0.01 Pascal-seconds (Pa s), for example between about 0.01 to about 1,000, or between about 0.01 to about 100, or between about 0.01 to about 50, or between about 0.01 to about 20, or between about 0.1 to about 15, or between about 1 to about 10 Pascal-seconds (Pa s), including each integer within the specified range. In various embodiments, the viscosity of the suspension is sufficient to avoid sedimentation or segregation of the solids therein.

The term "gel-forming agent" as used herein refers to various gelling and viscosity agents, solution binders, thickeners, and/or emulsifiers, with each possibility representing a separate embodiment. In some embodiments, the gel-forming agent when released, at least in part, into the aqueous medium forms a gel-like consistency thereby increasing the viscosity of the aqueous medium. It is believed that the gel-like consistency is formed by a network or skeleton of polymeric chains of the gel-forming agent, which may be capable of supporting solid particles.

In certain aspects and embodiments, the gel-forming agent comprises a non-ionic, cationic, or anionic gel-forming polymer, or combinations or mixtures thereof. In one embodiment, the gel-forming agent comprises a non-ionic gel-forming polymer. In other embodiments, the gel-forming agent comprises a cationic gel-forming polymer. In yet other embodiments, the gel-forming agent comprises an anionic gel-forming polymer.

Non-limiting examples of non-ionic gel-forming polymers which are suitable for use in certain embodiments include HPMC (hydroxypropyl methylcellulose), HPC (hydroxypropyl cellulose), hydroxyethyl cellulose, hydroxymethyl cellulose, gelatin, povidone (PVP: polyvinyl pyrrolidone) and the like, with each possibility representing a separate embodiment. In one embodiment, the non-ionic gel-forming polymer comprises HPMC. It is contemplated that different grades of HPMC such as, but not limited to, K15M, K4M, E4M and the like, are included within the scope of the present disclosure.

Non-limiting examples of cationic gel-forming polymers which are suitable for use in certain embodiments include gelatin, zein, albumin, casein, and cationic polysaccharides such as chitosan and the like, with each possibility representing a separate embodiment.

Non-limiting examples of anionic gel-forming polymers which are suitable for use in certain embodiments include anionic polysaccharides and carboxy polysaccharides such as sodium alginate, alginic acid, pectin, hyaluronic acid, polyglucuronic acid (poly-α—and —β—1,4—glucuronic acid), polygalacturonic acid (pectic acid), chondroitin sulfate, carrageenan, furcellaran, anionic gums and the like, with each possibility representing a separate embodiment.

Currently preferred gel-forming agents include, but are not limited to, at least one of the following: polysaccharides, acrylic or methacrylic polymers, cellulose derivatives, polyethylene glycol, alginic acid, sodium alginate, carbomers, gelatin, magnesium aluminum silicate, poloxamers, polyvinyl alcohol, and naturally occurring or synthetic gums. Each possibility represents a separate embodiment. The naturally occurring or synthetic gums are typically selected from xanthan gum, gum arabic, guar gum, locust bean gum, and gellan gum. Each possibility represents a separate embodiment. In one embodiment, the naturally occurring or synthetic gum comprises xanthan gum. In further embodiments, the cellulose derivatives are selected from microcrystalline cellulose, carboxy methyl cellulose, or a mixture thereof. Each possibility represents a separate embodiment.

According to certain aspects and embodiments, the amount of the gel-forming agent in the plurality of units is in the range of from about 5% to about 50% (w/w) of the total weight of the plurality of units, including each integer within the specified range. Preferably, the amount of the gel-forming agent in the plurality of units is in the range of from about 10% to about 40% (w/w) of the total weight of the plurality of units, including each integer within the specified range. In some embodiments, the amount of the gel-forming agent is about 5%, about 7%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, or about 50% (w/w) of the total weight of the plurality of units, with each possibility representing a separate embodiment.

In some embodiments, the outer coating comprising a gel-forming agent substantially covers the cores. In one embodiment, the outer coating covers the cores by at least about 25% of the surface area. In particular embodiment, the outer coating covers the cores by at least about 25%, about 30%, about 35%, about 40%, about 45%, about 50%, about 55%, about 60%, about 65%, about 70%, about 75%, about 80%, about 85%, about 90%, about 95%, or about 100% (substantially complete coverage) of the surface area, with each possibility representing a separate embodiment.

According to certain aspects and embodiments, the composition may further comprise a second population comprising a plurality of particles, preferably wherein the plurality of particles comprise a gel-forming agent. The gel-forming agent may be the same or different from the gel-forming agent in the outer coating of the first population, with each possibility representing a separate embodiment. According to certain aspects and embodiments, the amount of the gel-forming agent in the second population, if present, is in the range of from about 5% to about 50% (w/w) of the total weight of the composition, including each integer within the specified range. Preferably, the amount of the gel-forming agent in the second population, if present, is in the range of from about 10% to about 40% (w/w) of the total weight of the composition, including each integer within the specified range. In some embodiments, the amount of the gel-forming agent in the second population is about 5%, about 7%, about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, or about 50% (w/w) of the total weight of the composition, with each possibility representing a separate embodiment. The total weight of the composition, as used herein, refers to the weight of the plurality of units, including the active ingredient and all applied coatings and excipients in addition to the weight of the plurality of particles when present.

In further aspects and embodiments, the composition disclosed herein further comprises one or more excipients. It is contemplated that the excipients may constitute the inert seeds and/or are incorporated into the various coating layers described herein.

Suitable excipients include, but are not limited to, a binder, a filler, a surfactant, an anti-tacking agent, a plasticizer, a lubricant, a glidant, a disintegrant, an alkaline substance, a diluent, a tonicity enhancing agent, a wetting agent, a buffering substance, a colorant, a preservative, and any combination thereof, with each possibility representing a separate embodiment.

Suitable binders within the scope of the present disclosure include, but are not limited to, polyvinylpyrrolidone, copovidone, hydroxypropylmethyl cellulose, hydroxypropyl cellulose, starch, gelatin, or sugars. Each possibility represents a separate embodiment. Sugars include sucrose, dextrose, molasses, and lactose, with each possibility representing a separate embodiment.

Suitable fillers within the scope of the present disclosure include, but are not limited to, sugars such as lactose, sucrose, mannitol or sorbitol and derivatives therefore (e g amino sugars), ethylcellulose, microcrystalline cellulose, silicified microcrystalline cellulose and the like, with each possibility representing a separate embodiment.

Suitable surfactants within the scope of the present disclosure include, but are not limited to, non-ionic, anionic or cationic surfactants. Typically, surfactants may have one lipophilic and one hydrophilic group in the molecule. The surfactant may optionally comprise one or more of soaps, detergents, emulsifiers, dispersing and wetting agents. Each possibility represents a separate embodiment. More specifically, surfactants may optionally comprise, for example, one or more of polysorbate, stearyltriethanolamine, sodium lauryl sulfate, sodium taurocholate, laurylaminopropionic acid, lecithin, benzalkonium chloride, benzethonium chloride and glycerin monostearate; and hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose among others, with each possibility representing a separate embodiment.

Suitable anti-tacking agents within the scope of the present disclosure include, but are not limited to, magnesium stearate, calcium stearate, stearic acid, talc, mica, colloidal silicon, and the like among others, with each possibility representing a separate embodiment.

Suitable plasticizers within the scope of the present disclosure include, but are not limited to, cetyl alcohol, dibutyl sebacate, polyethylene glycol, polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol, and sorbitol among others, with each possibility representing a separate embodiment.

Suitable lubricants within the scope of the present disclosure include, but are not limited to, sodium stearyl fumarate, stearic acid, polyethylene glycol, or stearates, such as magnesium stearate, with each possibility representing a separate embodiment.

A suitable glidant within the scope of the present disclosure is e.g., colloidal silicon dioxide.

Suitable disintegrants within the scope of the present disclosure include, but are not limited to, crospovidone, croscarmelose sodium, a sugar alcohol, a cellulose derivative, cross-linked derivatives of starch (e.g. sodium starch glycolate), pregelatinized starch, crosslinked sodium carboxymethyl cellulose, low substituted hydroxypropylcellulose, and any combination or mixture thereof, with each possibility representing a separate embodiment. Additional disintegrants include, but are not limited to, silicates, carbonates, polyoxyethylene sorbitan fatty acid esters, stearic monoglyceride, guar gum, and lactose. Each possibility represents a separate embodiment. Suitable sugar alcohols include, but are not limited to, mannitol, sorbitol, maltitol, xylitol, and any combination or mixtures thereof. Each possibility represents a separate embodiment. Additional sugar alcohols include, but are not limited to, arabitol, isomalt, erythritol, glycerol, lactitol, and mixtures thereof. Each possibility represents a separate embodiment. Suitable cellulose derivatives include, but are not limited to, methylcellulose, cross-linked carboxylic methylcelluloses, microcrystalline cellulose, and any combination or mixture thereof. Each possibility represents a separate embodiment.

In order to stabilize the drug substance, which is susceptible to degradation in acidic environment, the proton pump inhibitor may be mixed with an alkaline substance. Suitable alkaline substances include, but are not limited to, organic and inorganic alkaline substances, with each possibility representing a separate embodiment. Suitable organic alkaline substances include, but are not limited to, basic amino acids such as arginine and lysine, amine derivatives and salts, amino sugars such as meglumine, salts of stearic acid such as sodium stearate and the like, with each possibility representing a separate embodiment. Suitable inorganic alkaline substances include, but are not limited to, hydroxides such as sodium or potassium hydroxide, carbonates such as calcium, magnesium or zinc carbonate, and the like, with each possibility representing a separate embodiment.

Suitable diluents include, but are not limited to, dicalcium phosphate, sugars, lactose, calcium phosphate, cellulose, kaolin, mannitol, sodium chloride, and dry starch, with each possibility representing a separate embodiment.

Suitable tonicity enhancing agents are selected from ionic and non-ionic agents. Each possibility represents a separate embodiment. For example, ionic compounds include, but are not limited to, alkali metal or alkaline earth metal halides, such as, for example, $CaCl_2$ KBr, KCl, LiCl, NaI, NaBr or NaCl, or boric acid. Each possibility represents a separate embodiment. Non-ionic tonicity enhancing agents are, for example, urea, glycerol, sorbitol, mannitol, propylene glycol, or dextrose, with each possibility representing a separate embodiment.

Suitable wetting agents include, but are not limited to, glycerin, starches, and the like. Each possibility represents a separate embodiment.

Suitable buffering substances include, but are not limited to, acidic buffering agents such as short chain fatty acids, citric acid, acetic acid, hydrochloric acid, sulfuric acid, and fumaric acid, with each possibility representing a separate embodiment; and basic buffering agents such as tris, sodium carbonate, sodium bicarbonate, sodium hydroxide, potassium hydroxide and magnesium hydroxide, with each possibility representing a separate embodiment.

Suitable colorants include, but are not limited to, alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide, with each possibility representing a separate embodiment.

Examples of preservatives are quaternary ammonium salts such as benzalkonium chloride, benzoxonium chloride or polymeric quaternary ammonium salts, alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sorbic acid or ascorbic acid, with each possibility representing a separate embodiment.

In specific embodiments, the composition disclosed herein comprises a plurality of units, each comprising: (i) a core comprising (a) a proton pump inhibitor in an amount of about 1% to about 15% by weight; (b) a subcoating in an amount of about 5% to about 25% by weight; (c) an enteric coating in an amount of about 10% to about 40% by weight; (ii) an outer coating comprising a gel-forming agent, the gel-forming agent in an amount of about 10% to about 40% by weight; and (iii) at least one excipient selected from a binder, a filler, a surfactant, an anti-tacking agent, a plasticizer, a lubricant, a glidant, a disintegrant, an alkaline substance, a diluent, a tonicity enhancing agent, a wetting agent, a buffering substance, a colorant, a preservative, and any combination thereof in an amount of from about 0% to about 60% by weight, wherein presence of all components add to 100%. It is understood by those skilled in the art that any integer within the specified ranges is included within the scope of the disclosure.

In some embodiments, the composition disclosed herein comprises:

a plurality of cores that include inert seeds, a drug coating layer, and optional subcoating, enteric coating and/or taste-masking:

the inert seeds comprising a filler, e.g. sugar spheres, microcrystalline cellulose particles, and/or lactose spheres;

the drug coating layer covering the inert seeds comprising a proton-pump inhibitor, e.g. esomeprazole magnesium; an alkalizing agent, e.g. meglumine; a binder, e.g. hydroxypropylmethyl cellulose (HPMC), hydroxypropyl cellulose (HPC), and/or polyvinylpyrrolidone (PVP); and optionally a surfactant, e.g. polysorbate; and/or a filler, e.g. mannitol;

an optional subcoating layer covering the drug-coated seeds comprising a binder, e.g. hydroxypropylmethyl cellulose (HPMC), hydroxypropyl cellulose (HPC), and/or polyvinylpyrrolidone (PVP); an anti-tacking agent, e.g. talc; and optionally a surfactant, e.g. polysorbate and/or a filler, e.g. mannitol;

an optional enteric coating covering the drug-coated seeds (with or without subcoating) comprising one or more enteric coating polymers, e.g. hydroxypropyl methylcellulose phthalate (HPMCP), and/or hydroxypropyl methyl cellulose acetate succinate (HPMCAS), and/or poly (meth)acrylic acid based polymers; an anti-tacking agent, e.g. talc; a plasticizer, e.g. cetyl alcohol and/or triethyl citrate; and optionally a colorant, e.g. titanium dioxide;

an optional taste-masking layer covering the enteric coating or the subcoating or the drug-coated seeds comprising a taste-masking polymer, e.g. a methacrylate-based copolymer; and a glidant, e.g. colloidal silicon dioxide; and an outer coating covering the cores (with or without subcoating, enteric coating, and/or taste-masking layer) comprising a gel-forming agent, e.g. xanthan gum; a binder, e.g. hydroxypropylmethyl cellulose (HPMC), hydroxypropyl cellulose (HPC), and/or polyvinylpyrrolidone (PVP); and a colorant, e.g. yellow iron oxide;

the composition may optionally further comprise a plurality of particles as a second population comprising inert seeds comprising a filler, e.g. sugar spheres, microcrystalline cellulose particles, and/or lactose spheres; and a coating covering the inert seeds comprising a gel-forming agent, e.g. xanthan gum; a binder, e.g. hydroxypropylmethyl cellulose (HPMC), hydroxypropyl cellulose (HPC), and/or polyvinylpyrrolidone (PVP); and a colorant, e.g. yellow iron oxide.

The compositions disclosed herein can be manufactured using conventional processes as is known in the art such as, but not limited to, spheronization, milling, de-agglomeration, precipitation, and/or crystallization, with each possibility representing a separate embodiment. In certain embodiments, the composition is prepared by applying an outer coating comprising a gel-forming agent to cores comprising a therapeutically effective amount of a PPI. In additional embodiments, the cores are prepared by applying a drug-containing layer (in the form of a solution or dispersion) to inert seeds. Optionally a subcoating in the form of a solution or dispersion can be applied to the drug-coated seeds followed by the application of an enteric coating over the subcoating or the drug-containing layer. The enteric coating may be applied in the form of an organic or aqueous solution or dispersion, with each possibility representing a separate embodiment. In certain embodiments, the outer coating comprising a gel-forming agent is applied to the cores in the form of an aqueous solution or dispersion, with each possibility representing a separate embodiment. In various embodiments, the outer coating comprising a gel-forming agent is applied to the cores in the form of organic-based solution or dispersion, with each possibility representing a separate embodiment. In particular embodiments, the outer coating comprising a gel-forming agent is applied to the cores in the form of an alcohol (e.g. ethanol, isopropyl alcohol and the like) solution or dispersion, with each possibility representing a separate embodiment. The application of the various coatings may be performed as is known in the art using standard equipment such as, but not limited to, a fluid bed coater (e.g. a Wurster coater or a rotary bed coater), extruder, or spray dryer. When using spray coating technique, various apparatus may be employed including, but not limited to, rotary disks, single-fluid high pressure swirl nozzles, two-fluid nozzles or ultrasonic nozzles, Single stage dryer, Two stage dryer, Horizontal dryer, Fluidized spray coater (e.g., TURBOJET), Multi stage drier, Compact spray dryer, Integrated filter drier, FILTERMAT® dryer, including, e.g., Glatt, Gea-Niro, BWI Malin, or Allgaier among others, with each possibility representing a separate embodiment. After applying the coatings, the units may be admixed with particles comprising at least one excipient comprising a gel-forming agent.

In an exemplary embodiment, the composition of the disclosure is prepared according to the following steps:(a) applying a therapeutically effective amount of a proton pump inhibitor and optionally a pharmaceutically acceptable excipient onto inert seeds to obtain drug-coated seeds; (b) optionally applying a subcoating onto the drug-coated seeds; (c) applying an enteric coating onto the drug-coated seeds obtained in step (a) or the subcoating of the drug-coated seeds obtained in step (b) to obtain cores; (d) applying an outer coating comprising a gel-forming agent onto the cores obtained in step (c) to obtain units as disclosed herein; and (e) optionally blending the units obtained in step (d) with particles comprising at least one excipient comprising a gel-forming agent. Optionally, the method of preparing the composition disclosed herein further involves additional processing steps including, but not limited to heating, drying, sieving, and lubricating as is known in the art.

In certain aspects and embodiments, the composition disclosed herein may be adapted for preparing a single dose sachet. However, it is contemplated that other solid dosage forms (e.g. capsules, cachets or sprinkle dosage forms) can be suitable according to the embodiments of the disclosure. It is contemplated that by using a single population of units as disclosed herein or first and second populations as disclosed herein, a substantially uniform composition suitable for large scale partitioning into solid dosage forms, such as single dose sachets, can be obtained. This is afforded, at least in part, due to a substantially uniform size distribution of the units and particles of the disclosure. In some embodiments, the plurality of units and the plurality of particles of the second population, if present, have a size ranging from about 100 µm to about 1,500 µm, including each integer within the specified range. In other embodiments, the units and the particles of the second population, if present, have a size ranging from about 200 µm to about 1,300 µm, including each integer within the specified range. In further embodiments, the units and the particles of the second population, if present, have a size ranging from about 300 µm to about 1,100 µm, including each integer within the specified range. In additional embodiments, the units and the particles of the second population, if present, have a size ranging from about 400 µm to about 1,000 µm, including each integer within the specified range. In certain embodiments, the units and the particles of the second population, if present, have a mean size of about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 µm, about 950 µm, about 1,000 µm, about 1,050 µm, about 1,100 µm, about 1,150 µm, about 1,200 µm, about 1,250 µm, about 1,300 µm, about 1,350 µm, about 1,400 µm, about 1,450, or about 1,500 µm. Each possibility represents a separate embodiment. In one embodiment, the composition is suitable for oral administration. It is contemplated that the composition disclosed herein may be in any form suitable for oral administration including, but not limited to, granules, pellets, or powder for oral suspension. Each possibility represents a separate embodiment. In another embodiment, the composition is suitable for administration using a nasogastric tube.

The composition of the present disclosure is useful for inhibiting gastric acid secretion. In one embodiment, the composition of the present disclosure is used in the treatment of gastroesophageal reflux disease, gastritis, peptic ulcers (duodenal and gastric), or erosive esophagitis, with each possibility representing a separate embodiment.

Accordingly, provided herein is a method of treating a disease or disorder including, but not limited to, gastroesophageal reflux disease, gastritis, peptic ulcers (duodenal and gastric), and erosive esophagitis, the method comprising administering to a subject in need thereof the composition of the present disclosure. The subject in need thereof is typically a mammal, preferably a human. It is contemplated that other diseases or disorders associated with excessive acid secretion e.g. Zollinger-Ellison syndrome can be treated using the composition of the disclosure. The amount of a composition to be administered depends on various factors including, but not limited to, the subject being treated (age and gender) and the severity of the disease being treated, and can be determined by the judgment of the prescribing physician. Because of patient-to-patient variability, dosages are a guideline only and the physician may adjust doses of the compounds to achieve the level of effective treatment that the physician considers appropriate for the patient. In considering the degree of treatment desired, the physician must balance a variety of factors such as, but not limited to, the age of the patient and the presence of other diseases or conditions. The compositions of the present disclosure may contain any dosage of the proton pump inhibitor, for example from about 2 mg to about 50 mg of the active ingredient such as, but not limited to, 2.5 mg, 5 mg, 10 mg, 20 mg, 30 mg, or 40 mg. Each possibility represents a separate embodiment.

The term "therapeutically effective amount" or "an effective amount" as used herein refers to a quantity of a compound which is sufficient to provide a beneficial effect to the subject to which the compound is administered. The effective amount can be determined by any one of ordinary skill in the art and can be tested on various models both in vitro and in vivo.

The term "treating" as used herein refers to stopping or slowing down the progression of the disease. The term "treating" further includes the reduction in the occurrence of various symptoms associated with gastric acid secretion. This term also encompasses prevention for prophylactic situations or for those individuals who are susceptible to developing e.g. gastric or duodenal ulcers.

As used herein and in the appended claims, the term "about" refers to ±10%.

As used herein and in the appended claims, the singular forms "a", "an", and "the" include plural references unless the context clearly dictates otherwise. Thus, for example, reference to "a layer" includes a plurality of such layers and equivalents thereof known to those skilled in the art, and so forth. It should be noted that the term "and" or the term "or" are generally employed in its sense including "and/or" unless the context clearly dictates otherwise.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

A composition according to certain embodiments of the disclosure was prepared as follows: Inert sugar spheres seeds were coated with a drug layer containing esomeprazole (in an amount equivalent to 20 mg). A subcoating layer containing HPMC (hypromellose) and an enteric coating layer containing hypromellose phthalate or hypromellose acetate succinate as the enteric polymer were then sequentially applied followed by the application of an outer coating containing xanthan gum to obtain units (active pellets).

Exemplary formulations within the scope of the present disclosure are outlined in Tables 1-9 below:

TABLE 1

| Substance | mg/composition |
|---|---|
| Esomeprazole magnesium | 21.7 |
| Sugar spheres | 21.0 |
| Hypromellose (HPMC E5) | 20.5 |
| Talc | 11.9 |

TABLE 1-continued

| Substance | mg/composition |
|---|---|
| Hypromellose phthalate | 61.5 |
| Cetyl alcohol | 11.1 |
| Triethyl citrate (TEC) | 5.2 |
| Titanium dioxide | 1.3 |
| Xanthan gum | 37.8 |
| Polyvinylpyrrolidone | 14.0 |
| Total | 206 |

TABLE 2

| Substance | mg/composition |
|---|---|
| Esomeprazole magnesium | 21.7 |
| Sugar spheres | 21.0 |
| Hypromellose (HPMC E5) | 20.5 |
| Talc | 10.5 |
| Hypromellose phthalate | 47.0 |
| Cetyl alcohol | 8.5 |
| Triethyl citrate (TEC) | 4.0 |
| Titanium dioxide | 1.0 |
| Xanthan gum | 117.6 |
| Polyvinylpyrrolidone | 44.0 |
| Total | 295.8 |

TABLE 3

| Substance | mg/composition |
|---|---|
| Esomeprazole magnesium | 21.7 |
| Sugar spheres | 21.0 |
| Hypromellose (HPMC E5) | 20.5 |
| Talc | 6.5 |
| Hypromellose phthalate | 47.0 |
| Cetyl alcohol | 8.5 |
| Triethyl citrate (TEC) | 4.0 |
| Titanium dioxide | 1.0 |
| Xanthan gum | 67.1 |
| Polyvinylpyrrolidone | 44.7 |
| Polysorbate | 2.0 |
| Mannitol | 20.0 |
| Meglumine | 5.0 |
| Total | 269 |

TABLE 4

| Substance | mg/composition |
|---|---|
| Esomeprazole magnesium | 21.7 |
| Sugar spheres | 21.0 |
| Hypromellose (HPMC E5) | 20.5 |
| Talc | 11.9 |
| Hypromellose phthalate | 61.5 |
| Cetyl alcohol | 11.1 |
| Triethyl citrate (TEC) | 5.2 |
| Titanium dioxide | 1.3 |
| Xanthan gum | 47.3 |
| Polyvinylpyrrolidone | 18.0 |
| Citric acid | 0.5 |
| Total | 220 |

TABLE 5

| Substance | mg/composition |
|---|---|
| Esomeprazole magnesium | 21.7 |
| Sugar spheres | 21.0 |
| Hypromellose (HPMC E5) | 20.5 |
| Talc | 10.5 |
| Hypromellose phthalate | 47.0 |
| Cetyl alcohol | 8.5 |
| Triethyl citrate (TEC) | 4.0 |
| Titanium dioxide | 1.0 |
| Xanthan gum | 58.8 |
| Polyvinylpyrrolidone | 22.0 |
| Total | 215 |

TABLE 6

| Substance | mg/composition |
|---|---|
| Esomeprazole magnesium | 21.7 |
| Sugar spheres | 21.0 |
| Hypromellose (HPMC E5) | 20.5 |
| Talc | 19.8 |
| Hypromellose acetate succinate | 46.1 |
| Triethyl citrate (TEC) | 9.2 |
| Xanthan gum | 40.0 |
| Polyvinylpyrrolidone | 14.8 |
| Total | 193.1 |

TABLE 7

| Substance | mg/composition |
|---|---|
| Esomeprazole magnesium | 22.3 |
| Sugar spheres | 21.0 |
| Hypromellose (HPMC E5) | 20.5 |
| Talc | 10.5 |
| Hypromellose phthalate | 47.0 |
| Cetyl alcohol | 8.5 |
| Triethyl citrate (TEC) | 4.0 |
| Titanium dioxide | 1.0 |
| Xanthan gum | 150.0 |
| Polyvinylpyrrolidone | 150.0 |
| Polysorbate | 2.0 |
| Mannitol | 7.0 |
| Ferric oxide yellow | 1.0 |
| Total | 444.8 |

TABLE 8

| Substance | mg/composition |
|---|---|
| Esomeprazole magnesium | 22.3 |
| Sugar spheres | 21.0 |
| Hypromellose (HPMC E5) | 20.5 |
| Talc | 10.5 |
| Hypromellose phthalate | 47.0 |
| Cetyl alcohol | 8.5 |
| Triethyl citrate (TEC) | 4.0 |
| Titanium dioxide | 1.0 |
| Xanthan gum | 150.0 |
| Hydroxypropylcellulose | 85.7 |
| Polysorbate | 2.0 |
| Mannitol | 7.0 |
| Total | 379.5 |

TABLE 9

| Substance | mg/composition |
|---|---|
| Esomeprazole magnesium | 22.3 |
| Sugar spheres | 21.0 |
| Hypromellose (HPMC E5) | 20.5 |
| Talc | 10.5 |
| Hypromellose phthalate | 47.0 |
| Cetyl alcohol | 8.5 |
| Triethyl citrate (TEC) | 4.0 |
| Titanium dioxide | 1.0 |
| Xanthan gum | 71.9 |
| Polyvinylpyrrolidone | 71.9 |
| Polysorbate | 2.0 |
| Mannitol | 7.0 |
| Total | 287.6 |

Example 2

A composition according to certain embodiments of the disclosure was prepared as follows: Inert sugar spheres seeds were coated with a drug layer containing esomeprazole (in an amount equivalent to 5 mg or 40 mg). A subcoating layer containing HPMC (hypromellose) and an enteric coating layer containing hypromellose phthalate as the enteric polymer were then sequentially applied followed by the application of an outer coating containing xanthan gum. The obtained units (active pellets) were then mixed with a second population of pellets (inert pellets) containing microcrystalline cellulose or sugar spheres coated with an outer coating containing xanthan gum.

Exemplary formulations within the scope of the present disclosure are outlined in Tables 10-14 below:

TABLE 10

| Substance | mg/composition |
|---|---|
| Pellets containing PPI | |
| Esomeprazole magnesium | 43.4 |
| Sugar spheres | 42.0 |
| Hypromellose (HPMC E5) | 41.0 |
| Talc | 13.0 |
| Hypromellose phthalate | 94.0 |
| Cetyl alcohol | 17.0 |
| Triethyl citrate (TEC) | 8.0 |
| Titanium dioxide | 2.0 |
| Xanthan gum | 134.2 |
| Polyvinylpyrrolidone | 89.4 |
| Polysorbate | 4.0 |
| Mannitol | 40.0 |
| Meglumine | 10.0 |
| Inert pellets | |
| Microcrystalline cellulose | 145.8 |
| Xanthan gum | 152.1 |
| Polyvinylpyrrolidone | 101.4 |
| Ferric oxide yellow | 0.8 |
| Total | 938.1 |

TABLE 11

| Substance | mg/composition |
|---|---|
| Pellets containing PPI | |
| Esomeprazole magnesium | 5.4 |
| Sugar spheres | 5.3 |
| Hypromellose (HPMC E5) | 5.1 |

TABLE 11-continued

| Substance | mg/composition |
|---|---|
| Talc | 1.6 |
| Hypromellose phthalate | 11.8 |
| Cetyl alcohol | 2.1 |
| Triethyl citrate (TEC) | 1.0 |
| Titanium dioxide | 0.3 |
| Xanthan gum | 16.8 |
| Polyvinylpyrrolidone | 11.2 |
| Polysorbate | 0.5 |
| Mannitol | 5.0 |
| Meglumine | 1.3 |
| Inert pellets | |
| Sugar spheres | 36.4 |
| Xanthan gum | 38.0 |
| Polyvinylpyrrolidone | 25.3 |
| Ferric oxide yellow | 0.2 |
| Total | 167.3 |

TABLE 12

| Substance | mg/composition |
|---|---|
| Pellets containing PPI | |
| Esomeprazole magnesium | 43.4 |
| Sugar spheres | 42.0 |
| Hypromellose (HPMC E5) | 41.0 |
| Talc | 13.0 |
| Hypromellose phthalate | 94.0 |
| Cetyl alcohol | 17.0 |
| Triethyl citrate (TEC) | 8.0 |
| Titanium dioxide | 2.0 |
| Xanthan gum | 134.2 |
| Polyvinylpyrrolidone | 89.4 |
| Polysorbate | 4.0 |
| Mannitol | 40.0 |
| Meglumine | 10.0 |
| Inert pellets | |
| Sugar spheres | 127.6 |
| Xanthan gum | 133.1 |
| Polyvinylpyrrolidone | 88.7 |
| Ferric oxide yellow | 0.7 |
| Total | 888.1 |

TABLE 13

| Substance | mg/composition |
|---|---|
| Pellets containing PPI | |
| Esomeprazole magnesium | 5.4 |
| Sugar spheres | 5.3 |
| Hypromellose (HPMC E5) | 5.1 |
| Talc | 1.6 |
| Hypromellose phthalate | 11.8 |
| Cetyl alcohol | 2.1 |
| Triethyl citrate (TEC) | 1.0 |
| Titanium dioxide | 0.3 |
| Xanthan gum | 16.8 |
| Polyvinylpyrrolidone | 11.2 |
| Polysorbate | 0.5 |
| Mannitol | 5.0 |
| Meglumine | 1.3 |
| Inert pellets | |
| Microcrystalline cellulose | 36.4 |
| Xanthan gum | 38.0 |
| Polyvinylpyrrolidone | 25.3 |
| Ferric oxide yellow | 0.4 |
| Total | 167.5 |

TABLE 14

| Substance | mg/composition |
|---|---|
| Pellets containing PPI | |
| Esomeprazole magnesium | 43.4 |
| Sugar spheres | 42.0 |
| Hypromellose (HPMC E5) | 41.0 |
| Talc | 13.0 |
| Hypromellose phthalate | 94.0 |
| Cetyl alcohol | 17.0 |
| Triethyl citrate (TEC) | 8.0 |
| Titanium dioxide | 2.0 |
| Xanthan gum | 134.2 |
| Polyvinylpyrrolidone | 89.4 |
| Polysorbate | 4.0 |
| Mannitol | 40.0 |
| Meglumine | 10.0 |
| Inert pellets | |
| Microcrystalline cellulose | 127.6 |
| Xanthan gum | 133.1 |
| Polyvinylpyrrolidone | 88.7 |
| Ferric oxide yellow | 1.4 |
| Total | 888.8 |

Example 3

Figure 2:
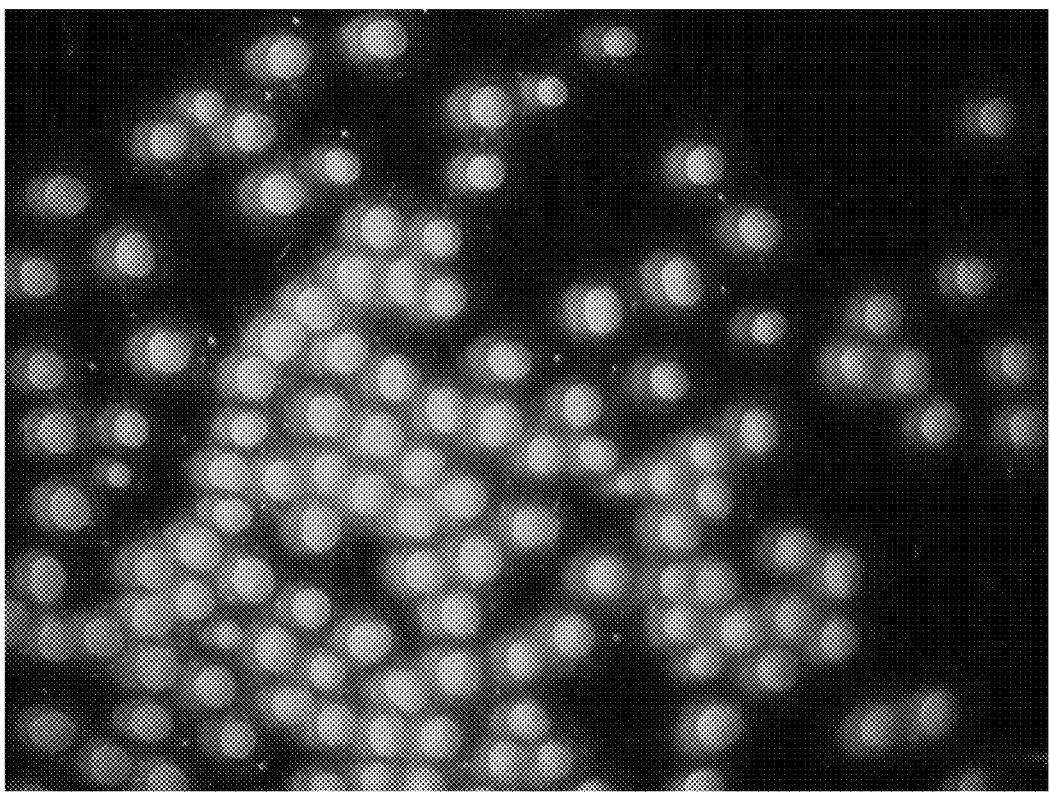
FIG. 2. A micrograph showing a plurality of units according to the disclosure as set forth in Table 3 after admixture with tap water.
Figure 3A:
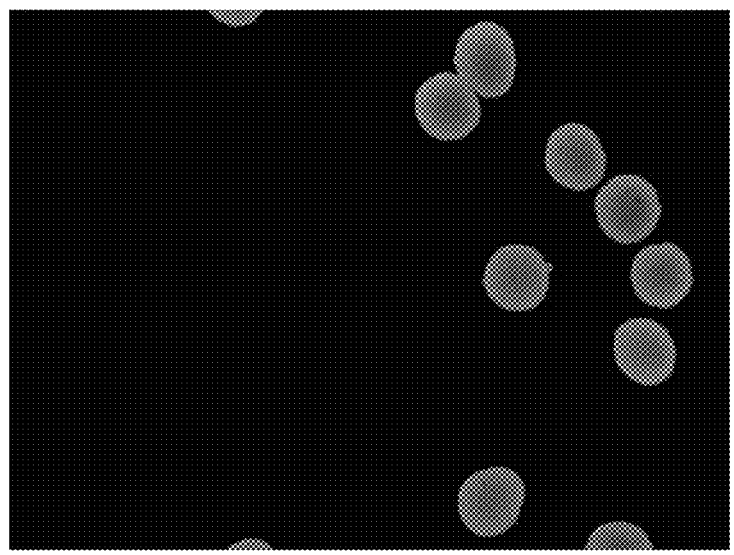
FIGS. 3A-3E. A sequence of micrographs showing a plurality of units according to the disclosure as set forth in Table 7 after admixture with tap water at times 0 (3A), 100 seconds (3B), 200 seconds (3C), 300 seconds (3D), and 600 seconds (3E).
Figure 3B:
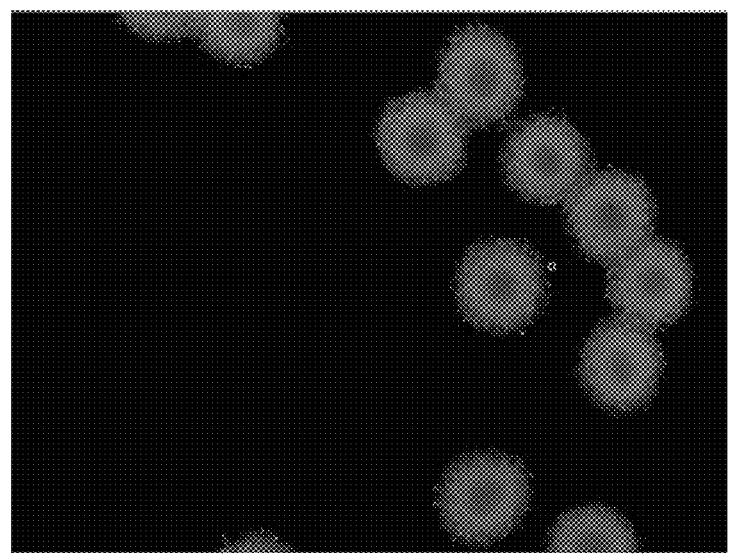
Figure 3C:
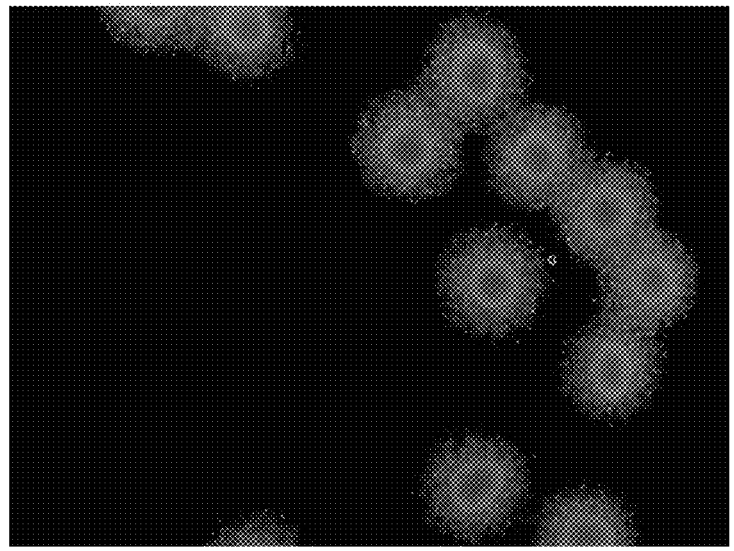
Figure 3D:
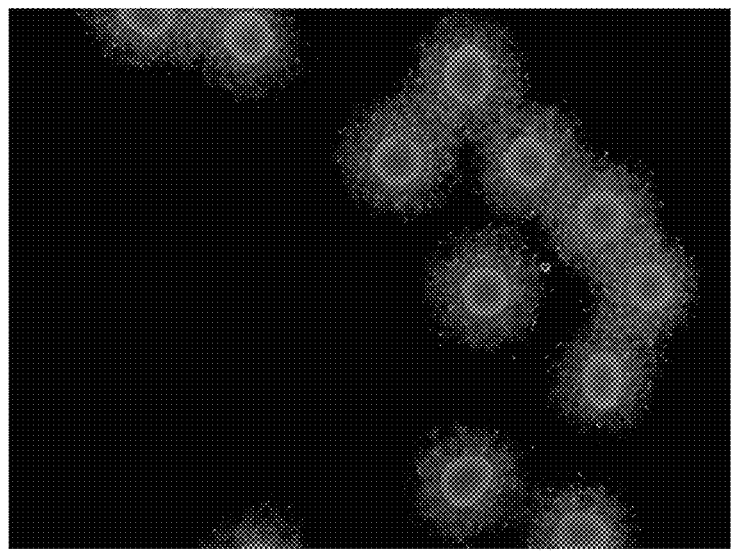
Figure 3E:
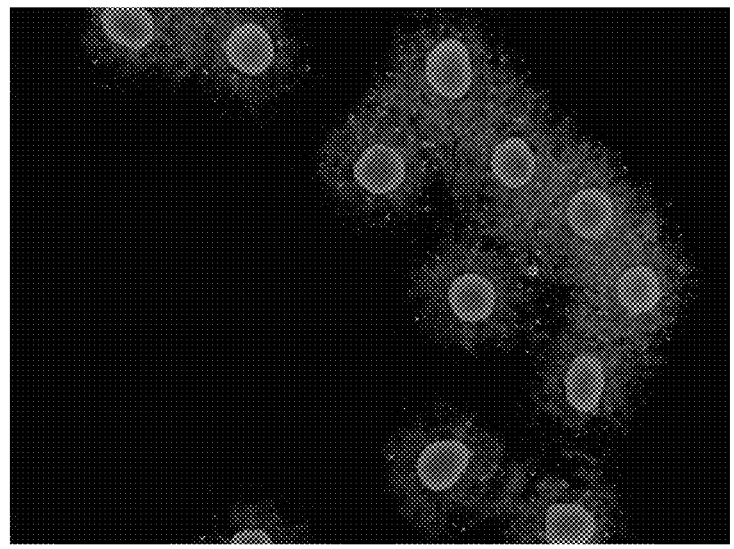
Figure 4:
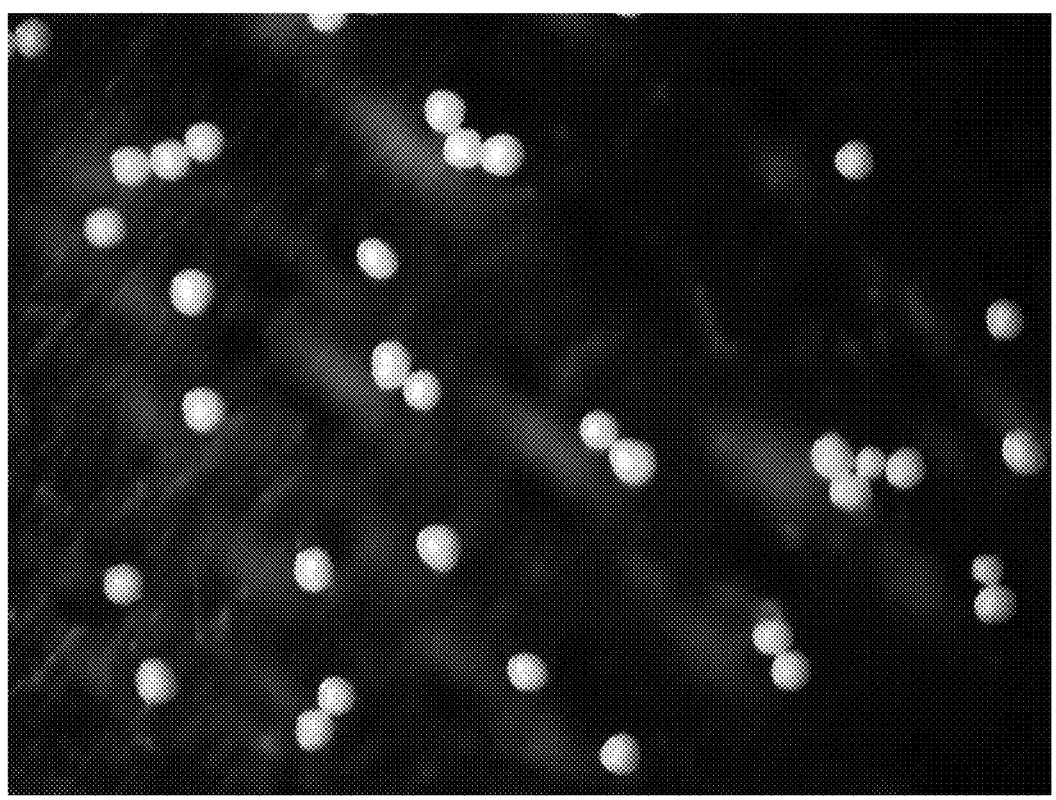
FIG. 4. A micrograph showing control units after admixture with tap water.
Figure 5A:
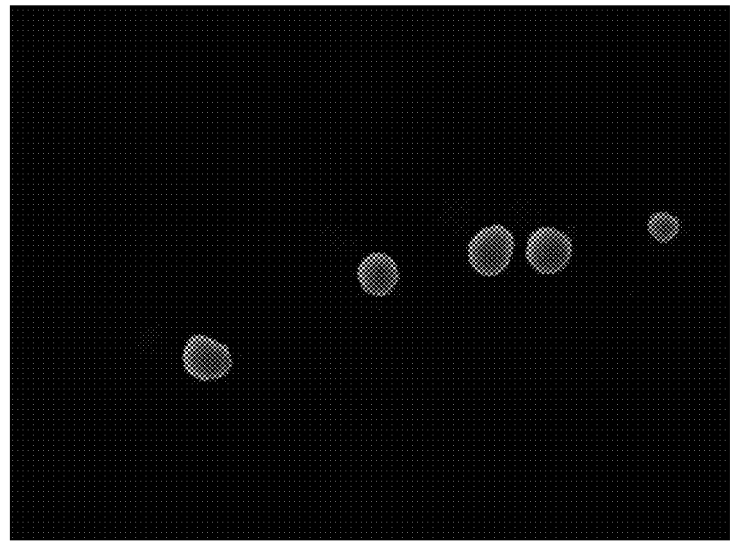
FIGS. 5A-5B. A sequence of micrographs showing control units after admixture with tap water at times 0 (5A), and 600 seconds (5B).
Figure 5B:
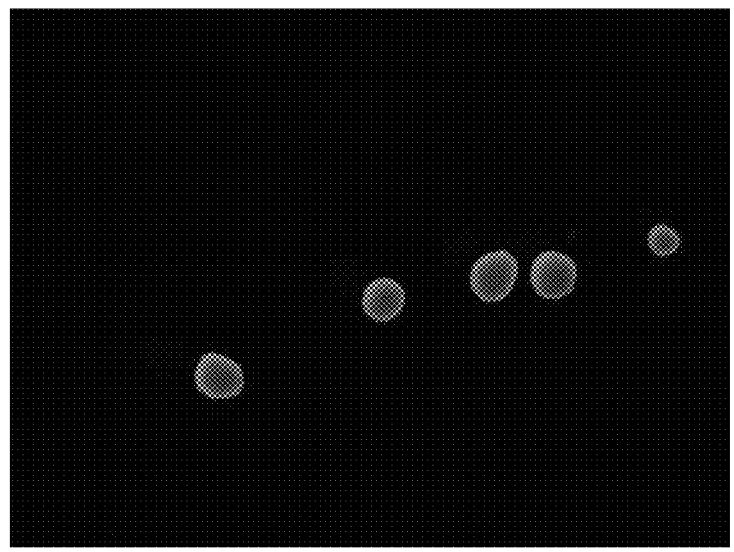

A composition according to certain embodiments of the disclosure was mixed with tap water and placed on a Petri dish. The same procedure was performed on a composition with no xanthan gum outer coating (control). FIGS. 1 and 2 show micrographs of the compositions according to certain embodiments of the disclosure as set forth in Tables 2 and 3, respectively, exemplifying the halo formed around each pellet. The halo is indicative of imbibition of water by the outer coating and its swelling. FIGS. 3A-3E show a sequence of micrographs of the composition according to certain embodiments of the disclosure as set forth in Table 7, the micrographs taken at time 0, 100, 200, 300 and 600 seconds after admixture with tap water, respectively. The micrographs exemplify the swelling of the outer coating due to imbibition of water. FIG. 4 shows the absence of halo in a control sample and FIGS. 5A and 5B show the absence of a halo in a control sample at time 0 and 600 seconds after admixture with tap water, respectively.

Example 4

Figure 6A:
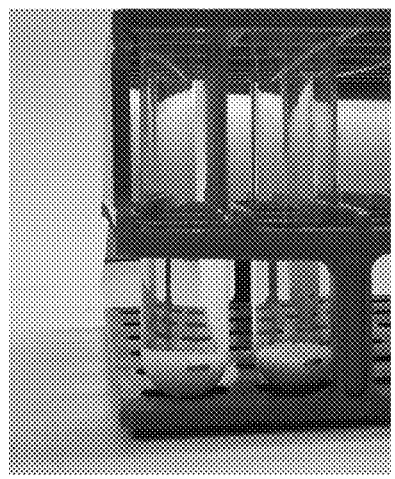
FIGS. 6A-6B. Pictures showing a plurality of units according to the disclosure as set forth in Table 2 (on the right) and control units that do not contain an outer-coating (on the left) before (6A) and after (6B) admixture with tap water.
Figure 6B:
Figure 7A:
FIGS. 7A-7B. Pictures showing a plurality of units according to the disclosure as set forth in Table 3 (on the right) and control units that do not contain an outer-coating (on the left) before (7A) and after (7B) admixture with tap water.
Figure 7B:
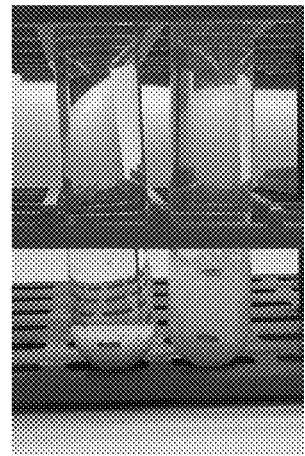

Approximately 550 mg of a composition according to certain embodiments of the disclosure were placed in a glass tube (16×150 mm) and the initial height occupied by the composition was marked. 15 ml of tap water were injected into the tube and the height occupied by the composition was marked again after 1-2 minutes. The same amount of a composition without an outer coating of xanthan gum (control) was placed in another glass tube and subjected to the same procedure. FIGS. 6 and 7 show photographs of the tubes demonstrating the swelling of the units containing xanthan gum due to imbibition of water (right tubes). Initial height occupied by the compositions: 0.6 cm (FIGS. 6A and 7A corresponding to the compositions as set forth in Tables 2 and 3, respectively; right tube). Height occupied by the compositions after admixture with tap water: 2 cm (FIG. 6B corresponding to the composition as set forth in Table 2; right tube) and 1.8 cm (FIG. 7B corresponding to the composition as set forth in Table 3; right tube). The height occupied by the control remained unchanged (FIGS. 6A, 7A, 6B and 7B; left tube). Since the increase in volume is directly proportional to the increase in height, the swelling (increase in volume) of compositions according to embodiments of the disclosure is at least 233% and 200%, respectively, of the initial volume.

While certain embodiments of the invention have been illustrated and described, it will be clear that the invention is not limited to the embodiments described herein. Numerous modifications, changes, variations, substitutions and equivalents will be apparent to those skilled in the art without departing from the

The invention claimed is:

1. A composition suitable for forming a viscous suspension upon admixing with an aqueous medium, the composition comprising a plurality of swellable units, wherein each unit of said plurality of swellable units comprises:
   i) a core comprising a proton pump inhibitor;
   ii) an enteric coating layer over the core; and
   iii) a swellable outer coating comprising a gel-forming agent over the enteric coating layer,
   wherein each of said plurality of swellable units is coated with said swellable outer coating such that it is designed to swell upon imbibition of the aqueous medium by at least 50% of its initial volume.

2. The composition of claim 1, wherein the plurality of swellable units swells upon imbibition of the aqueous medium by at least 100% of its initial volume.

3. The composition of claim 2, wherein the plurality of swellable units swells upon imbibition of the aqueous medium by at least 150% of its initial volume.

4. The composition of claim 1, wherein the proton pump inhibitor comprises at least one of omeprazole, lansoprazole, pantoprazole, rabeprazole, tenatoprazole, and pharmaceutically acceptable salts thereof.

5. The composition of claim 4, wherein the proton pump inhibitor comprises s-omeprazole magnesium.

6. The composition of claim 1, wherein the core comprises an inert seed coated with a drug layer comprising a proton pump inhibitor.

7. The composition of claim 1, wherein the enteric coating comprises at least one polymer selected from the group consisting of cellulose acetate phthalate (CAP), hydroxypropyl methylcellulose phthalate (HPMCP), hydroxypropyl methylcellulose acetate succinate (HPMCAS), polyvinyl acetate phthalate, cellulose acetate trimellitate, shellac, polymethacrylic acid, polymethyl methacrylate, polyethyl methacrylate, polyethyl acrylate, and mixtures thereof.

8. The composition of claim 1, wherein the gel-forming agent comprises at least one of polysaccharide, acrylic or methacrylic polymer, cellulose derivative, polyethylene glycol, alginic acid, sodium alginate, carbomer, gelatin, magnesium aluminum silicate, poloxamer, polyvinyl alcohol, and naturally occurring or synthetic gum.

9. The composition of claim 8, wherein the naturally occurring or synthetic gum is selected from the group consisting of xanthan gum, gum arabic, guar gum, locust bean gum, and gellan gum.

10. The composition of claim 9, wherein the naturally occurring or synthetic gum comprises xanthan gum.

11. The composition of claim 1, wherein each unit further comprises a pharmaceutically acceptable excipient.

12. The composition of claim 11, wherein the pharmaceutically acceptable excipient comprises at least one of a binder, a filler, a surfactant, an anti-tacking agent, a plasticizer, a lubricant, a glidant, a disintegrant, an alkaline substance, a diluent, a tonicity enhancing agent, a wetting agent, a buffering substance, a colorant, a preservative, and any combination thereof.

13. The composition of claim 1 further comprising a plurality of particles.

14. The composition of claim 13, wherein the plurality of particles is selected from granules, inert pellets, beads, powder, and mixtures thereof.

15. The composition of claim 14, wherein the plurality of particles comprises a gel-forming agent.

16. The composition of claim 15, wherein the gel-forming agent comprises at least one of polysaccharide, acrylic or methacrylic polymer, cellulose derivative; polyethylene glycol, alginic acid, sodium alginate, carbomer, gelatin, magnesium aluminum silicate, poloxamer, polyvinyl alcohol, and naturally occurring or synthetic gum.

17. The composition of claim 16, wherein the naturally occurring or synthetic gum is selected from the group consisting of xanthan gum, gum arabic, guar gum, locust bean gum, and gellan gum.

18. The composition of claim 17, wherein the naturally occurring or synthetic gum comprises xanthan gum.

19. The composition of claim 15, wherein the plurality of particles further comprises a pharmaceutically acceptable excipient.

20. The composition of claim 19, wherein the pharmaceutically acceptable excipient comprises at least one of a binder, a filler, a surfactant, an anti-tacking agent, a plasticizer, a lubricant, a glidant, a disintegrant, an alkaline substance, a diluent, a tonicity enhancing agent, a wetting agent, a buffering substance, a colorant, a preservative, and any combination thereof.

21. The composition of claim 1, adapted for preparing a single dose sachet.

22. The composition of claim 1, adapted for administration via the oral route or a nasogastric tube.

23. A method of treating a disease or disorder selected from the group consisting of gastroesophageal reflux disease, gastritis, peptic ulcers (duodenal and gastric), and erosive esophagitis, the method comprising administering to a subject in need thereof the composition of claim 1.

24. The composition of claim 1, wherein the gel-forming agent is in an amount of about 10% to about 40% by weight of each unit.

* * * * *